(12) United States Patent
Latham

(10) Patent No.: US 9,526,701 B2
(45) Date of Patent: Dec. 27, 2016

(54) SUSTAINED DRUG RELEASE AND IMPROVED PRODUCT STABILITY USING NON-COVALENT PARTICLE COATING METHODS

(71) Applicant: Keith R. Latham, Abingdon, VA (US)

(72) Inventor: Keith R. Latham, Abingdon, VA (US)

(*) Notice: Subject to any disclaimer, the term of this patent is extended or adjusted under 35 U.S.C. 154(b) by 85 days.

(21) Appl. No.: 13/721,733

(22) Filed: Dec. 20, 2012

(65) Prior Publication Data
US 2013/0157992 A1 Jun. 20, 2013

Related U.S. Application Data

(60) Provisional application No. 61/577,738, filed on Dec. 20, 2011.

(51) Int. Cl.
*A61K 9/14* (2006.01)
*A61K 9/20* (2006.01)

(52) U.S. Cl.
CPC ............ *A61K 9/14* (2013.01); *A61K 9/146* (2013.01); *A61K 9/2031* (2013.01); *A61K 9/2054* (2013.01); *A61K 9/2063* (2013.01)

(58) Field of Classification Search
CPC ........ A61K 9/14; A61K 9/146; A61K 9/2031; A61K 9/2054; A61K 9/2063
See application file for complete search history.

(56) References Cited

U.S. PATENT DOCUMENTS

| | | | |
|---|---|---|---|
| 2,380,970 A * | 8/1945 | Kitter | 53/428 |
| 3,549,524 A | 12/1970 | Haller | |
| 3,632,739 A * | 1/1972 | Kornblum | 424/465 |
| 5,008,114 A * | 4/1991 | Lovrecich | 424/484 |
| 5,225,204 A * | 7/1993 | Chen | A61K 47/4823 424/451 |
| 5,767,227 A | 6/1998 | Latham | |
| 5,910,569 A | 6/1999 | Latham | |
| 7,018,654 B2 | 3/2006 | Kirk | |
| 2002/0128177 A1 | 9/2002 | Kirk | |
| 2005/0266067 A1 | 12/2005 | Sengupta | |
| 2007/0065514 A1* | 3/2007 | Howell | 424/489 |
| 2007/0078119 A1* | 4/2007 | Purro et al. | 514/185 |
| 2007/0099841 A1* | 5/2007 | Moncrief et al. | 514/17 |
| 2007/0232529 A1 | 10/2007 | Mickle | |
| 2008/0051450 A1* | 2/2008 | Santini | A61K 9/0019 514/449 |
| 2009/0130202 A1 | 5/2009 | Smith | |
| 2010/0130723 A1 | 5/2010 | Latham | |
| 2010/0137639 A1 | 6/2010 | Latham | |
| 2011/0142941 A1* | 6/2011 | Davis et al. | 424/489 |
| 2012/0065267 A1* | 3/2012 | Ehrenkranz et al. | 514/567 |

FOREIGN PATENT DOCUMENTS

| | | | |
|---|---|---|---|
| GB | 634398 | * | 3/1950 |
| WO | 2005025543 | | 3/2005 |
| WO | 2011084620 | | 7/2011 |

OTHER PUBLICATIONS

Federal Register, vol. 62, No. 157, pp. 43535-43538 1997.*
Protein Purification Process Engineering, R. G. Harrison, Ed., 1994, pp. 148-171.*
Lyophilization of Biopharmaceuticals, H. R. Costantino & M. J. Pikal, Eds., 2004, pp. 192-195.*
Baccarin et al., Ethylcellulose Microspheres containing Sodium Diclofenac: Development and Characterization, Acta Farm. Bonaerense 25 (3):40104 (2006).*
Yokoi et al., Flocculation Properties of Poly(γ-Glutamic Acid) Produced by Bacillus subtilis, Jl. of Ferm. and Bioengineering, vol. 82, No. 1, 84-87, 1996.*
Constantino et al. Lyophilization of Biopharmaceuticals. American Association of Pharmaceutical Scientists. pp. 192-195.. 2004.*
Reinhard Vehring, Pharmaceutical Particle Engineering via Spray Drying, Pharm. Res. vol. 25, No. 5, May 2008 (published online Nov. 28, 2007).*
Freitas et al., Ultrasonic atomization into reduced pressure atmosphere,—envisaging aseptic spray-drying for microencapsulation, J. Controlled Release, 95 (2004) 185-195.*
L.R. Snyder, Classification of the Solvent Properties of Common Liquids, J Chromatogr Sci (1978) 16 (6): 223-234.*
Ambrogi et al., Microporous material from kanemite for drug inclusion and release, II Farmco, 56 (2001) 421-425.*
Beretzky et al., Pelletization of Needle-Shaped Phenylbutazone Crystals, Jl. Therm. Anal. and Calor., vol. 69 (2002) 529-539.*
Johansen and Moller, Solvent Deposition Method for Enhancement of Dissolution Rate: Importance of Drug-to-Excipient Ratio, Jl. Pharm. Sci., vol. 67, No. 1, Jan. 1978, pp. 134-136.*
Excipient Development for Pharmaceutical, Biotechnology and Drug Delivery, Kaldare and Chaubal, Eds., Informa Healthcare USA, Inc. 2006, p. 103 section.*
Mihranyan et al., Influence of cellulose powder structure on moisture-induced degradation of acetylsalicyclic acid, Eur. J. Pharm. Sci., 27 (2006) 220-225.*

(Continued)

*Primary Examiner* — Karlheinz R Skowronek
*Assistant Examiner* — Joseph Fischer
(74) *Attorney, Agent, or Firm* — Stockwell & Smedley, PSC

(57) ABSTRACT

The present invention relates to improved methods of making compositions and compositions made by these methods having improved stability and/or extended release of an active agent or drug upon administration. These compositions may generally comprise an active agent or drug non-covalently immobilized or bound to an excipient substrate. The active agent or drug may include a wide variety of drugs. Binding of the active agent or drug to the substrate may be achieved by evaporating a solvent containing the active agent dissolved therein or by triggering co-precipitation by addition of a precipitating solvent. Additional steps of vacuum removal of surrounding atmosphere and replacement with inert gas may provide additional stability. Present methods and compositions also facilitate manufacturing of drug products and may make these processes safer in some cases. The present invention further provides improved methods of treatment or administration, which may take advantage of improvements with present compositions.

41 Claims, 4 Drawing Sheets

(56) References Cited

OTHER PUBLICATIONS

Mihranyan et al., Sorption of nicotine to cellulose powders, Eur. J. Pharm. Sci., 22 (2004) 279-286.*
Toth et al., The effect of solvent concentration on the separation of radioiodine labelled triiodothyronine and thyroxine by adsorption chromatography, Radiochemical and Radioanalytical Letters; v. 29(4) p. 207-213; May 10, 1977 (Toth, Abstract only is provided).*
International Search Report (ISR) and Written Opinion for PCT/US12/70894.
Cavaliere et al., "Serum Levels of Total Testosterone and Sex Hormone Binding Globulin in Hypothyroid Patients and Normal Subjects Treated with Incremental Doses of L-T4 or L-T3." Journal of Andrology. Jun. 30, 1988, vol. 9, No. 3, pp. 215-219.
Laitinen, R.L. et al., "Perphenazine solid dispersions for orally fast-disintegrating tablets . . .", Drug Dev. and Ind. Pharm., 36(5): 601-613 (2010).
Modi, A. et al., "Enhancement of Dissolution Profile by Solid Dispersion (Kneading) Technique", AAPS PharmSciTech 7(3): E1-E6 (2006).
Kumar, M.A. et al., "Development and Evaluation of Solid Dispersion Formulated Ibuprofen Tablets using Cyclodextrins as Carrier", IJPRD, 3(11): 93-101 (2012).
Chaulang, g. et al., "Preparation and Characterization of Solid Dispersion Tablet of Furosemide with Crospovidone", Research J. Pharm and Tech, 1(4): 386-389 (2008).
Jadhav, S.B. et al., "Formulation and Evaluation of Dispersible Tablets of Diltiazem Hydrochloride", Int'l J. of PharmTech Research, 3(3): 1314-1321 (2011).
Jaskirat, S. et al., "Solubility Enhancement by Solid Dispersion Method: A Review", J. of Drug Delivery & Therapeutics, 3(5): 148-155 (2013).

* cited by examiner

| Dissolution Time (min.) | BCT303 (Lot 3030134) | | Cytomel® (Lot 60210) | |
|---|---|---|---|---|
| | HPLC T3 Area | % Dose (50 μg) | HPLC T3 Area | % Dose (50 μg) |
| 0 | 0 | 0 | 0 | 0 |
| 10 | 14 | 28 | 36 | 72 |
| 20 | – | – | 41 | 82 |
| 30 | 19 | 38 | – | – |
| 40 | – | – | 48 | 96 |
| 60 | 31 | 62 | 42 | 84 |
| 120 | 41 | 82 | 36 | 72 |
| 180 | 47 | 94 | – | – |
| 270 | 48 | 96 | 33 | 66 |

FIG. 1

| Elapsed Time (Hr) | T3 (ng/dL) | TSH (μIU/ml) |
|---|---|---|
| −1 | 99.6 | 4.080 |
| 0   (100 mcg dose) | | |
| 1.0 | 409.2 | 4.646 |
| 2.0 | 616.4 | 4.497 |
| 3.25 | 825.4 | 3.594 |
| 4.0 | 700.8 | 3.019 |
| 5.3 | 528.3 | 2.372 |
| 6.7 | 461.8 | 2.101 |
| 23.5 | 188.3 | 0.841 |
| 27.6 | 165.8 | 0.735 |
| 52.0 | 105.6 | 0.630 |
| 72.0 | 103.2 | 0.660 |

T3 Normal Range: 80.0 − 204 ng/dL
TSH Normal Range: 0.350 − 4.500 μIU/mL

FIG.3

Results (30 mcg dose/day)

| Test | Units | Reference Range | Pre-Dose | 3 Weeks | 6 Weeks |
|---|---|---|---|---|---|
| TSH | μIU/mL | 0.350 – 4.500 | 4.681 | 2.950 | 0.955 |
| TT3 | ng/dL | 80.0 – 204.0 | 42.4 | 128.2 | 130.00 |
| TT4 | μg/dL | 5.0 – 12.5 | 5.1 | 3.9 | 1.9 |
| T3 Uptake | % | 22.5 – 37.0 | 34.0 | 33.0 | 37.5 |
| Free T4 Index | – | 1.0 – 3.9 | 1.4 | 1.3 | 1.1 |
| Ferritin | ng/ml | 22 – 322 | 117 | 105 | 123 |
| Sex Hormone Binding Globulin | nmol/L | 13 – 71 | 23 | 27 | 36 |

FIG.4

SUSTAINED DRUG RELEASE AND IMPROVED PRODUCT STABILITY USING NON-COVALENT PARTICLE COATING METHODS

CROSS-REFERENCE TO RELATED APPLICATIONS

This application claims the benefit of priority to U.S. Provisional Patent Application No. 61/577,738, entitled "Sustained Drug Release and Improved Product Stability Using Non-Covalent Particle Coating Methods," filed on Dec. 20, 2011, the entire contents and disclosure of which are incorporated herein by reference.

BACKGROUND

Field of the Invention

The present invention relates to improved drug formulation methods, products formed by these methods, as well as methods of their use.

Background

Some formulated drug products are subject to chemical instability resulting in limited shelf life and potentially inaccurate drug dosing. In addition, sub-optimal rates of drug delivery to intended target tissues can result from uncontrolled drug release from the drug product. Overcoming these problems would enhance the safety and efficacy of many existing drug formulation products and new products in development.

In fact, multiple drug products have been recalled or withdrawn from the market due to low product stability. For example, products containing Liothyronine sodium, the L-isomer of triiodothyronine (T3), have had multiple recalls based on instability that resulted in lower than claimed dosing and possible formation of degradation products with unintended side effects. The brand name Cytomel® product (King/Pfizer) of Liothyronine sodium, as well as the generic version of Liothyronine sodium (Mylan, Watson and Paddock Laboratories) as referenced in the Abbreviated New Drug Applications (ANDAs) for these generic products, have all had documented problems with product stability and have been either recalled or withdrawn from the market. To claim substantial equivalence of the generic to the innovator product in the case of Cytomel®, the ANDA generic products were all required to be formulated with the same excipients (i.e., calcium sulfate, gelatin, starch, stearic acid, sucrose and talc) for bioequivalence and FDA approval. Therefore, it is not surprising that the equivalent generic product with the same Liothyronine formulation had similar instabilities as the reference drug. Likewise, multiple products other than Liothyronine sodium have also been recalled due to loss of potency.

Accordingly, there is a need in the art for improved drug formulation methods, and products formed thereby as well as uses thereof, that produce a homogeneous distribution of drug substances in a final drug product. There is also a need in the art for improved drug formulation methods that produce final drug products having a more consistent and controlled rate of drug release and/or enhanced product stability.

SUMMARY

According to a first broad aspect of the present invention, a method is provided comprising the following steps: (a) dissolving an active agent or drug in a solvent to form a solution containing the active agent or drug; and (b) evaporating the solvent from the solution until a substrate powder is formed, the substrate powder comprising the active agent or drug non-covalently bound to a substrate, wherein the substrate is a polymer or crystalline excipient.

According to a second broad aspect of the present invention, a method is provided comprising the following steps: (a) dissolving an active agent or drug in a dispersing solvent to form a solution containing the active agent or drug; (b) co-precipitating the active agent or drug and a substrate by adding a precipitating solvent to the solution to form a precipitate, the precipitate comprising the active agent or drug non-covalently bound to the substrate, wherein the substrate is a polymer or crystalline excipient.

According to a third broad aspect of the present invention, compositions are provided comprising the various substrate powders, final formulations, or dosage forms described herein.

According to a fourth broad aspect of the present invention, methods of treatment are provided based on new discoveries described herein and/or using the improved compositions of the present invention. A method is provided comprising the following steps: (a) administering a pharmaceutical composition to an individual, the pharmaceutical composition comprising a substrate powder, wherein the substrate powder comprises an active agent or drug non-covalently bound to a substrate, the substrate being a polymer or crystalline excipient.

BRIEF DESCRIPTION OF THE DRAWINGS

The accompanying drawings, which are incorporated herein and constitute part of this specification, illustrate exemplary embodiments of the invention, and, together with the detailed description herein, serve to explain features of the present invention.

FIG. 1 is a table showing the release properties of a T3 composition of the present invention relative to Cytomel®;

FIG. 3 is a table showing the time course of changes in blood levels of T3 and thyroid-stimulating hormone (TSH) following a single dosage of a T3 composition of the present invention; and FIG. 4 is a table showing blood levels of TSH, total T3 (TT3), total T4 (TT4), T3 uptake, free T4 index, ferritin and sex hormone binding globulin (SHBG).

DETAILED DESCRIPTION

Figure 2:
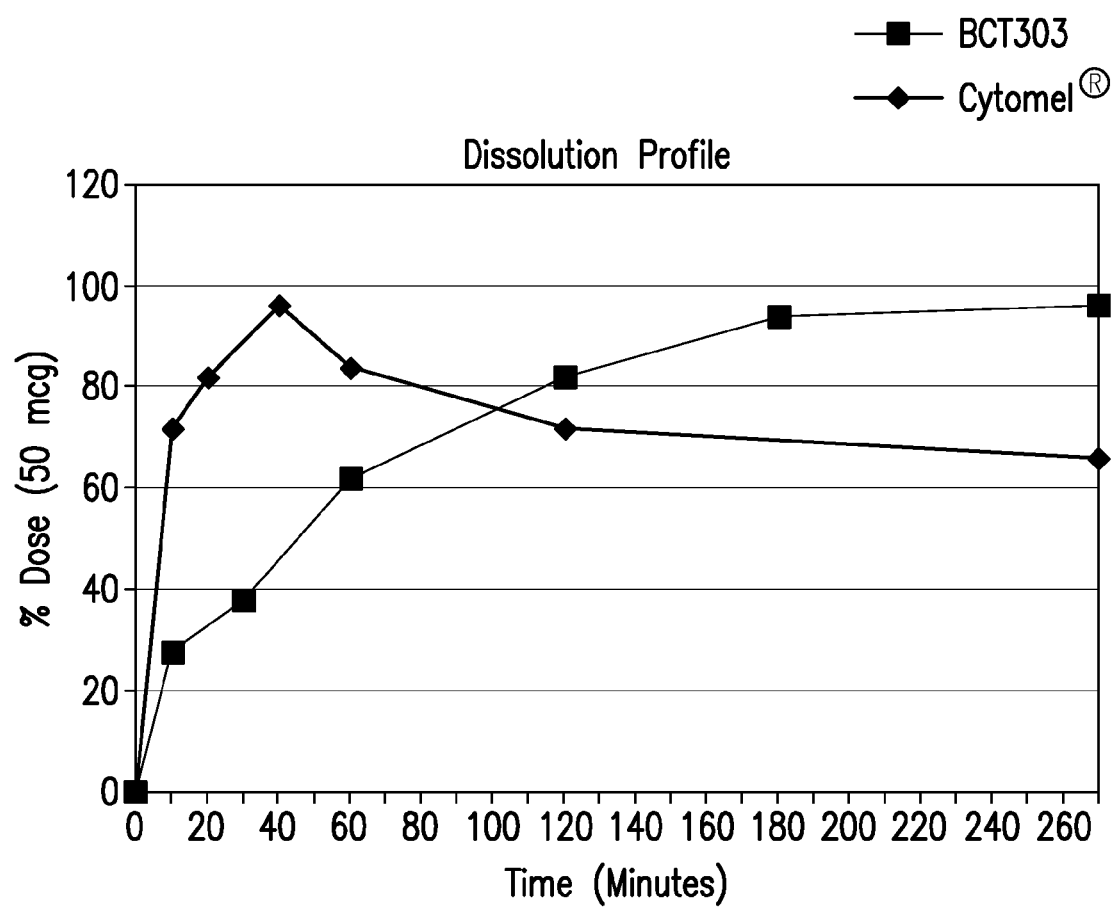
FIG. 2 is a time graph presenting the data from the table in FIG. 1.

Method embodiments of the present invention as described herein reduce product degradation (e.g., during storage) by immobilizing an active agent(s), ingredient(s) or drug(s) to a solid phase excipient or substrate that will be part of an eventual drug formulation that may be formed into tablets or other dosage formats. Embodiments of the present invention provide that a suitable solvent containing the active agent or drug and a solid phase substrate or excipient may be evaporated (e.g., under vacuum pressure and/or elevated temperature) to cause the active agent or drug to become non-covalently immobilized or bound to particles or granules of the excipient substrate. It is believed that the evaporation step of the present invention causes the active agent or drug to become immobilized, bound, coated, adhered, etc., to the solid phase substrate as the solvent evaporates due to intermolecular forces or interactions between the active agent/drug and the substrate. These intermolecular forces may include any intermolecular forces including hydrophobic interactions, hydrogen bonding, dipole-dipole, ionic, van der Waals, etc. In fact, unless the active agent/drug is incapable of binding to the substrate, this immobilization and interaction between the non-volatile active agent/drug and substrate may be forced to occur by methods of the present invention (at least somewhat) due to removal of the solvent. However, the strength of the binding, immobilization, etc., of the active agent or drug to the substrate will depend on the nature and extent of these intermolecular forces, which depend on the identity of the active agent/drug and substrate.

As will be explained further below, according to an alternative set of embodiments of the present invention, binding, immobilization, etc., of an active agent or drug to a substrate may instead be carried out by co-precipitation of the substrate and active agent or drug dissolved in the solvent by addition or introduction of a precipitating solvent into the solution.

According to embodiments of the present invention, non-covalent coating or immobilization of an active agent or drug to a selected excipient substrate is believed to stabilize the active agent or drug from degradation. Further stabilization of the product is also believed to occur by azeotropic and/or evaporative removal of contaminant components, like water and oxygen, during solvent evaporation, and the vacuum may be replaced with an inert, anhydrous gas like Nitrogen ($N_2$), Argon (Ar) or Xenon (Xe). Other displacement gases may also be used to achieve further advantages. For example, anhydrous carbon dioxide ($CO_2$) may be used as an inert replacement gas that may also serve an additional purpose of acidifying the local environment of a substrate for active agents or drugs that are more stable in acidic environments.

Multiple cycles of vacuum followed by replacement with inert gas to a desired specification may be used to produce a product having greater stability. In general, higher degrees of purity may be achieved with more removal/replacement cycles to remove volatiles and other molecules. As described herein, it is surprisingly found that immobilization of an active agent or drug to an excipient substrate followed by repeated rounds of vacuum and replacement with inert gas according to present method embodiments results in a product having increased stability and longer shelf-life (see, e.g., Example 3 below). Immobilization of an active agent or drug further leads to more consistent characteristics and more extended release of the active agent or drug when such a formulation is administered to an individual or patient (see, e.g., Examples 1 and 2 below).

Other molecules bound to, or associated with, drug compounds in final product formulations may contribute to product instability. Thus, it is theorized that removing or sequestering these molecules away from the active agent or drug in the final product formulation may lead to greater product stability and shelf-life. These molecules or ions may be left over from a previous synthesis or formulation step or may be inherited from preparations or sources of the substrate or active agent/drug. Many synthesized compounds or drugs have other molecules or ions associated with them, such as water and sodium, and many excipient substrates may also have volatiles associated with them. According to embodiments of the present invention, azeotropic and evaporative removal and sequestration of these so-called "contaminant" molecules may be achieved by the evaporation or vacuum removal step of the present invention to make a product formulation with the active agent or drug evenly distributed and immobilized to an excipient substrate away from these contaminant molecules. For removal of the solvent by evaporation, a reduced pressure or a standard vacuum may be used according to embodiments of the present invention. As stated above, in addition to improved stability, this evaporation step may also have the benefit of removing solvent and/or other molecules from a prior synthesis and immobilization step that may be problematic or toxic for later formulation or administration. This step may also be beneficial in removing or sequestering contaminants present from reagent sources or preparations of variable purity.

Example 4 below (describing immobilization of levothyroxine to a substrate) demonstrates advantages of the present invention over existing methods. Unlike Liothyronine, levothyroxine (T4) is normally supplied as the sodium salt with five water molecules bound to each molecule of thyroxine. Both water and sodium contribute to product instability. However, the method embodiment of the present invention as described in Example 4 below converts the levothyroxine to the anhydrous and sodium free form of the drug by "azeotroping" the bound water by vacuum removal and macro-distribution of the sodium to the excipient or substrate surface away from the immobilized levothyroxine. Thus, levothyroxine tablets may be produced by present methods that have enhanced stability with removal or sequestration of these contaminant molecules.

Production of drug products with homogeneous distribution of the active ingredients remains a fundamental formulation challenge for the pharmaceutical industry, especially for highly active drugs with low mass dosing in which small amounts of a drug are added or blended with large excipient volumes. During powder blending, small amounts of an active agent can become inadvertently partitioned to, or concentrated within, small compartments or portions of the formulation equipment surfaces due to particle size distribution and/or small dimensional irregularities and cavities on the surfaces of the blending equipment. In contrast, methods of the present invention, and products made thereby, have another advantage (in addition to increased stability) over existing formulations in that the distribution of the active agent or drug in the final product produced by present methods is substantially more homogeneous relative to mechanical mixing. By immobilization of the drug compound to the substrate from solution, the active agent or drug may be evenly distributed throughout the substrate before encountering equipment walls or surfaces or additional product components or ingredients.

According to some embodiments, an active agent or drug may be immobilized to a substrate as described herein to form a master mix of the substrate powder with the immobilized active agent/drug bound to the substrate, perhaps with other excipients. Such a master mix of the substrate powder may be concentrated relative to the final formulation that may be used to make the dosage form of the final drug product. See, e.g., Example 4 below for making a substrate immobilized Levothyroxine. Such a concentrated master mix may then be combined, blended, bulked up, etc., with one or more other compatible excipients to dilute the concentration of the active agent or drug in the master mix and make a larger volume of the final formulation. This master mix approach may be especially useful for drug products that have low mass quantities of the active agent or drug in the final formulation (i.e., present in small amounts in the final formulation). The concentrated master mix of the substrate powder may be made with a higher ratio of active agent or drug to substrate to facilitate blending and/or a higher degree of binding to individual excipient particles or granules of the substrate. By forming a concentrated master mix of the substrate powder, smaller volumes may be used in the immobilization step, which may also facilitate use or reduced or vacuum pressure and/or infusion of an inert gas during the evaporation/drying and blending process.

The present methods provide a facilitated method of achieving homogeneous distribution of the active agent or drug by initially dissolving the active agent or drug in a suitable solvent. The solution of the active agent or drug may be combined with a solid phase excipient or substrate, such as to form a suspension of the solid phase substrate. Although the excipient/substrate and the active agent or drug may be added to the solvent together (or the excipient/substrate may theoretically be added before the active agent or drug), it is generally preferred that the active agent or drug is first dissolved into the solvent prior to addition of the substrate. The latter approach allows for confirmation that the active agent/drug is in solution prior to addition of the substrate by confirmation that the solution has become clear (indicating that the active agent or drug is dissolved). Otherwise, it may be difficult to determine if the compound/drug is dissolved in a suspension or slurry containing the undissolved excipient substrate. However, although the substrate may often not be soluble and not become dissolved in the solvent/solution (to form a suspension or slurry with the solvent/solution) at this step, the substrate may alternatively become dissolved in the solvent at this step according to some embodiments as described further below.

Once the substrate and active agent or drug are present in the solvent (with at least the active agent or drug dissolved), the solvent may be removed by reduced pressure or vacuum evaporation to deposit, bind, immobilize, etc., the active agent or drug (uniformly distributed in solution) onto the solid phase surface of the substrate (including any interior porous surfaces of some substrates). The "reduced pressure" may be a pressure less than standard atmospheric pressure (e.g., less than about 30 inches of Hg). Thus, the homogeneously distributed active agent or drug in solution may become homogeneously distributed throughout, and immobilized to, the substrate as the solvent is removed. According to present methods, the homogeneous distribution of the active agent or drug in the final formulation as a result of binding or immobilizing of the active agent or drug to the substrate surface from solution will produce a more consistent drug product having more predictable characteristics for storage and/or eventual administration to an individual or patient.

Another advantage of embodiments of the present invention is that immobilization of the active agent or drug improves safety and ease of use during the manufacturing process. Certain drugs, especially those with high specific activity and potential for accidental toxic exposure, can be hazardous to manufacturing staff through powder inhalation and inadvertent ingestion or absorption through the skin and bodily membranes. Immobilization of these drugs to the solid phase excipient or substrate provides a valuable drug containment benefit that may be a significant improvement over, and/or adjunct to, standard containment methods. Moreover, as mentioned above, binding and immobilization of the active agent or drug to the substrate may help to avoid having the active agent or drug adhere or stick to the walls and surfaces of manufacturing equipment, which may be particularly important for compounds/drugs added in small amounts to much larger excipient volumes.

Although some of the present examples highlight the potential application of present methods to formulations containing Liothyronine or Levothyroxine (in addition to a few other examples), it is believed that the present methods and products are generally applicable to diverse groups of active agents and drugs. For purposes of the present invention, the terms "active agent" and "drug" refer jointly to any atom or compound that may be used as a nutritional ingredient, bioactive agent or drug in a composition for pharmaceutical or veterinary use. Since the methods and compositions of the present invention relate to non-covalent intermolecular interactions or forces between the active agent or drug and the excipient substrate to cause the active agent or drug to become immobilized or bound to the excipient substrate surface as part of the formulation process, compositions and methods of the present invention are broadly applicable to small molecule and small peptide drugs. Some examples may include steroids or corticosteroids, such as cortisol, cortisone, corticosterone, hydrocortisone, prednisone, prednisolone, methylprednisolone, betamethasone, etc., or other steroids, such as estrogen, etc., peptide and non-steroidal hormones, such as insulin, etc., thyroid hormones, such as thyroxine, triiodothyronine, etc., catecholamines or catecholamine precursors, such as dopamine, L-DOPA, DOPA Cyclocarbonate, etc., adrenergics, such as epinephrine, norepinephrine, etc., amino acids, such as tyrosine, cysteine, serine, etc., antibiotics, such as β-lactam antibiotics including penicillins, cephalosporins, etc., vitamins, such as vitamin A, vitamin E, etc., narcotics and opioids, such as methadone, morphine, amphetamine, etc., serotonergics, such as serotonin, etc., chemotherapies or cytotoxic drugs, such as methotrexate, etc., oxytocin, heparin, and many others. The active agent or drug may also include 3-monoiodo-L-tyrosine (MIT) and 3,5-diiodo-L-tyrosine (DIT). A person skilled in the art would recognize based on the disclosure and description provided herein that the present invention is generally applicable to a wide range of active agents or drugs given the many possible intermolecular interactions between an active agent/drug and the excipient particles of the substrate.

According to embodiments of the present invention, the active agent or drug may also include stereoisomers, such as a D- and L-isomer, of an active agent or drug. With regard to thyroid hormones and thyronine derivatives, the active agent or drug may include any L- or D-isomer of any iodinated thyronine congener. D-isomers of thyroid hormones may be converted into L-isomers of these hormones in the body. Among the iodinated L-thyronine congeners, the active agent or drug may include 3,5,3'-triiodo-L-thyronine (T3 or Liothyronine), 3,3',5'-triiodo-L-thyronine (Reverse T3 or rT3), and 3,5,3',5'-tetraiodo-L-thyronine or levo-thyroxine (T4).

The appropriate type of solvent and pharmaceutically acceptable substrate(s) to be used may depend on the chemical characteristics of the active agent(s) or drug(s) as well as the eventual formulation and dosage form of the product. While many solvents and solvent combinations are potentially suitable for the present invention, the choice of a suitable solvent may depend on the interaction of the solvent with the excipient substrate and the active agent or drug to be immobilized, bound, etc., onto the substrate. Generally speaking, preferable solvents may have relatively lower boiling points (e.g., at or below about 100° C.) to allow for their easier removal (e.g., under vacuum pressure) according to methods of the present invention relying on evaporative removal of the solvent. High purity solvents may also be preferred since they have a lower tendency to form peroxides or other reactive molecular species.

It is also generally preferred that the active agent or drug be soluble in the chosen solvent under conditions below the boiling point of the solvent, at least to an extent necessary for immobilization of the compound or drug to the excipient or substrate during the evaporation step of the present invention. However, the degree of solubility of an active agent or drug in a particular solvent may vary to a reasonable extent because larger volumes of solvent may be used to dissolve a less soluble active agent/drug since the volume of solvent may be subsequently removed by evaporation. The solvent may also preferably be compatible with the excipient or substrate to "wet" the surface of the excipient or substrate to allow for contact and immobilization of the active agent or drug to the substrate surface. In addition, it is generally preferred that the solvent used be chemically inert, such that the solvent will not easily react and form covalent chemical bonds with an excipient, substrate and/or the active agent or drug.

Since water retention may lead to product degradation with some types of active agents or drugs, the optimal solvent may be nearly anhydrous according to many embodiments to prevent such product degradation through water retention in the final product. In these embodiments, the solvent may also preferably have a capacity for azeotropic removal of water arising from other sources including product components. However, some water soluble compounds are best immobilized from an aqueous environment onto hydrophilic surfaces. Thus, water may also be used as a solvent or co-solvent according to some embodiments. Suitable solvents according to embodiments of the present invention may include tetrahydrofuran (THF), hexane, acetone, ethanol, methanol, methyl ethyl ketone, ethyl acetate, water and many others, depending on the specific application and the anticipated design of ternary interactions between the solvent, substrate (excipient) and drug or compounds to be immobilized.

According to some embodiments, two or more solvents may be used, especially for immobilization of two or more active agents or drugs having different solubilities. Although the two solvents may be used together or simultaneously, the two or more solvents may more preferably be used sequentially instead, such that a first solvent and solution containing a first active agent or drug and the substrate is first evaporated prior to addition of the second solvent containing a second active agent or drug. More preferably, only one solvent may be used if possible for co-immobilization of two or more active agents or drugs to the substrate(s) (see, e.g., Example 5 below involving co-immobilization of T3 and T4).

As an additional optional step, the active agent or drug may be re-suspended, or the substrate powder with the compound or drug immobilized to it may be washed, in a subsequent solvent that may be the same or different than the original solvent used in the present methods after evaporation of the original solvent. The active agent or drug may not be soluble in the subsequent solvent such that it remains bound to the substrate during such a wash step. This optional additional step may be done to remove residual water and/or to promote further product stability and/or purity. The subsequent solvent may then be removed and followed by replacement with inert gas as described herein.

For purposes of the present invention, the term "substrate" refers to a pharmaceutically suitable excipient that may be used to bind or immobilize an active agent or drug to its surface through intermolecular forces or interactions according to methods of the present invention. The optimal choice for a substrate may depend on the solvent and the active agent or drug, such that the active agent or drug may interact with and become immobilized to the substrate. The substrate may also be chosen depending on the final dosage form of the product. Any classic pharmaceutically acceptable excipient(s), such as micro-crystalline cellulose, etc., may be used as a substrate according to the present invention because they are considered (i) non-toxic, (ii) compatible with a wide range of solvents, and (iii) present a surface topology (e.g., porosity) and surface chemistry suitable for drug immobilization without covalent chemical interactions. Compounds or drugs immobilized to micro-crystalline cellulose, for example, are compatible with other excipients and may be blended with other excipients to make formulations that may be formed into tablets by direct compression. A micro-crystalline cellulose powder flow having the active agent or drug immobilized to it may also be used for filling capsules.

According to embodiments of the present invention, the substrate(s) that may be used for a given application may include a variety of polymer and crystalline excipients, such as cellulose and its derivatives (e.g., Avicel® and other equivalents), polydextrans (e.g., Sephadex®), controlled pore glass, porous silica, activated carbon, molecular sieves (e.g., potassium, sodium, or aluminum silicates), gelatins, polysaccharides, polypeptides, such as poly-tyrosine or poly-glutamic acid, starches, polyethylene glycols (PEG) and many others that are generally recognized as safe (GRAS), and combinations thereof. Many of these substrates may also be chemically modified to achieve further advantages. For example, the carboxy-methyl and amino derivatives of cellulose and agarose provide options and capabilities for chemical modification prior to binding of the active agent or drug. For a list of potentially suitable excipients that may be used as a substrate of the present invention, see, e.g., Rowe et al., Handbook of Pharmaceutical Excipients, Sixth Edition, *Pharmaceutical Press*, 2009, in addition to the references cited below and incorporated herein by reference.

Substrates with high porosity provide larger surface areas for immobilization, and binding of the active agent or drug to the interior porous surfaces of these substrates helps to further protect them against degradation by limiting exposure to the external environment. As a general rule, substrates should be selected having pore sizes that are at least larger than the molecular size of the active agent or drug. The higher surface area of porous substrates may also result in a higher percentage of the active agent or drug binding to the substrate without saturation given the much higher surface area of the porous substrate than the interior wall of the vessel holding the solution. In addition, binding of an active agent or drug to the interior porous surfaces of these substrates may also allow for a higher binding capacity and a higher order, diffusion limited release of the active agent or drug from the substrate when administered to an individual or patient. In other words, these substrate pores provide a large internal surface area and volume to regulate the release rate of the compound or drug through a combination of surface binding effects and limited diffusion rate (and possibly slowed bio-fluid accessibility) to result in an extended release of the compound or drug. Thus, these high surface area porous substrates contribute to higher loading capacity, greater stability and/or extended release.

Many substrates that may be used to immobilize the active agent or drug in formulations made according to methods of the present invention may preferably not be digested or dissolved when administered to an individual, such as in the stomach or intestinal lumen (i.e., the digestive tract) when administered orally to the individual. Therefore, cellulose and other non-digestable excipients may be used in these orally administered formulations such that the substrate remains intact in the digestive tract to restrain or extend the release of the active agent or drug from the substrate. However, in cases where extended release is not a concern (or immediate release is preferred), other substrates may be used for orally administered formulations that do become digested or dissolved in the stomach or lumen of the gut leading to more rapid release of the active agent or drug. Immobilization of the active agent or drug to such a digestable or dissolvable substrate in these cases may still provide the benefit of improved stability and longer shelf life during storage of the product even without extended release properties. Thus, substrates may also include polysaccharides and polypeptides, which are broken down in the digestive tract. Acceptable polymers like polyethylene glycol (PEG) are not digested but can provide a rapid release of the active agent or drug when administered by solubilization and conformation changes induced by a bio-fluid (see, e.g., Example 11 below). Similarly, other polymers, such as gelatin (i.e., denatured collagen), may provide a rapid release of the active agent or drug when administered orally by becoming digested when administered (see, e.g., Example 12 below).

According to embodiments of the present invention, one or more substrate(s) and one or more active agent(s) or drug(s) will be combined in the solvent typically without other excipients that might interfere with the selective immobilization, binding, etc., of the active agent(s)/drug(s) with the substrate(s). However, other excipients may be present in the solution, such as capping agents described below, especially if they do not interfere with the preferred and selective binding of the active agent(s)/drug(s) to the substrate(s). Upon evaporation, such as by vacuum pressure and/or elevated temperature, a powder of the substrate(s) with the active agent(s)/drug(s) immobilized to the substrate(s) will be formed, perhaps with one or more other excipients or capping agents. Following vacuum removal of the atmosphere or air surrounding the substrate powder, it may be replaced with an inert gas.

Once the substrate powder is formed by the immobilization step, the substrate powder with the immobilized active agent(s)/drug(s) bound thereto may be combined with other excipients to form a final formulation that may be used to make various dosage forms, such as by compression into tablets, etc., to form a final drug product, or the substrate powder with the immobilized active agent(s)/drug(s) may instead be placed into containers or vials for storage. Alternatively, the substrate powder with the immobilized active agent(s)/drug(s) formed by the immobilization step may not be combined with additional excipients and may itself comprise the final formulation that may be used to make various dosage forms that are the final drug product. Possible formulation methods according to the present invention are discussed further below.

These other excipients that may be combined with the substrate powder with the immobilized active agent(s) or drug(s) may include any pharmaceutically acceptable and suitable excipients or carriers that are known and used in existing drug formulations and may potentially include, for example, solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, fillers, diluents, disintegration agents, lubricants, sweetening agents, flavoring agents, dyes, glidants, wetting agents, etc., and combinations thereof. Possible dosage forms of the final drug product including the substrate powder with the immobilized active agent(s)/drug(s) therein may include solid dosage forms, such as powders, granules, tablets, pills, capsules, suppositories, depots, or dragee; or suitable liquid dosage forms, such as elixirs, syrups, suspensions, sprays, gels, lotions, creams, slurries, foams, jellies, ointments, salves, solutions, suspensions, tinctures, and/or emulsions. Because of their ease of administration, tablets and capsules may be preferably used as an oral dosage unit form when solid pharmaceutical compositions are employed. For additional description of pharmaceutical excipients, carriers, and dosage forms that may be suitable for use with the present invention, see, for example, Remington, *The Science and Practice of Pharmacy*, (University of the Sciences in Philadelphia, 21st ed., Lippincott Williams & Wilkins Co., 2005). See also, for example, U.S. Pat. Nos. 7,833,550, 7,390,808, 7,354,928, 7,348,325, 7,326,713, and 7,282,504, the contents and disclosures of which are incorporated herein by reference.

The non-covalent binding, immobilization, etc., of an active agent or drug to the surface of an excipient/substrate may be due to a variety of inter-molecular interactions or forces including any hydrophilic and/or hydrophobic interactions, such as hydrogen bonding, dipole-dipole, ionic, van der Waals, etc., or combinations thereof. Indeed, the relative contributions of these interactions between the excipient/substrate and active agent or drug over the surface area of the substrate may vary depending on the combination of solvent, active agent/drug, and substrate. These forces may be enhanced by the presence of the active agent or drug. Although binding or immobilization of the active agent or drug to the substrate is forced by evaporation of the solvent according to methods of the present invention, the strength or affinity of the non-covalent interaction between the active agent or drug and the substrate may vary depending on the nature and extent of these intermolecular forces or interactions. In fact, immobilization may occur in some cases even though the binding affinity between the active agent or drug and the substrate may be weak. Thus, the substrate may be chosen or determined empirically based on its binding affinity or strength to the active agent or drug to regulate or control the release properties and/or the stability of the formulation.

According to embodiments of the present invention, the sum of these intermolecular interactions between the substrate and the immobilized compound(s) or drug(s) may ultimately determine the release properties and bio-availability of the drug or compound immobilized to the substrate upon administration of the final product to an individual or patient. In general, a stronger affinity may lengthen or slow the time and rate of release of the compound/drug, whereas a weaker affinity will result in a faster rate of release. In addition to affecting release properties, a stronger affinity of the compound/drug for the substrate may also enhance product stability and minimize degradation. The rate of release of the active agent/drug from the substrate may also depend on the degree of porosity of the substrate and what proportion of the active agent or drug is bound to the interior pore surfaces of the substrate particles versus surfaces of substrate particles closer to or on the exterior surface of the substrate particles. The greater proportion of active agent or drug bound or immobilized to deep interior porous surfaces of the substrate particles should result in slower and more extended release when administered.

The bio-availability of the active agent or drug may also depend, for example, on the chemical characteristics of the bio-fluid or tissue environment to which the formulation is exposed in the body. In fact, as discussed further below, the affinity or binding strength of the compound or drug to the substrate may be chosen or modified by selecting the combination of solvent and excipient (and possibly controlling other factors) to create a product with a desired rate of release of the compound or drug when encountering a given bio-fluid or tissue environment according to its route of administration to fit therapeutic requirements for the drug. Delivery rate and bioavailability of the active agent or drug from the solid phase excipient or substrate may be controlled by the affinity of the compound or drug for the solid phase substrate, but also the solubility of the compound or drug in the surrounding bio-fluid (e.g., the acidic environment in the stomach or the higher pH environment in the lumen of the gut). Higher affinity will generally slow release (i.e., provide a more extended or sustained release), whereas higher solubility in the surrounding bio-fluid will increase the release rate.

The release of the active agent or drug may be further regulated by solid phase constraints in dissolution and diffusion of the compound or drug from porous structures and/or by the addition of other components, such as "capping agents," that may alter the interactions between the substrate and the active agent or drug immobilized to the substrate as well as the release rate of the active agent or drug. For purposes of the present invention, a "capping agent" refers to a substance other than the active agent or drug that binds to the substrate. Like the active agent or drug, the capping agent is "immobilized" to the substrate via intermolecular interactions or forces caused by precipitation or evaporation or vacuum removal of a solvent. A "capping agent" may generally be used to affect the binding, affinity, and/or release properties of an active agent or drug with a substrate.

The capping agent(s) of the present invention may be added to the solvent along with the excipient/substrate and the active agent or drug prior to removing the solvent for co-immobilization or co-binding with the active agent or drug to the substrate. Alternatively, an active agent or drug may be combined with a substrate in a first solvent to immobilize the active agent or drug to the substrate, which may be followed secondarily by adding the capping agent to a second solvent containing the substrate with the already immobilized active agent or drug to subsequently immobilize and bind the capping agent to the substrate. As yet another alternative, the capping agent may be added to a first solvent with the substrate to immobilize the capping agent to the substrate via evaporation of the solvent, which may be followed by addition of the "capped" substrate to a second solvent with an active agent or drug to immobilize the active agent or drug to the "capped" substrate in a subsequent immobilization step. The substrate powder formed by these processes with the bound active agent/drug and capping agent may then be stored or used to form a final drug product, which may involve subsequent formulation steps involving addition or blending of the substrate powder with other excipients.

Thus, capping agents may provide yet another way to affect, engineer or modulate the affinity of the active agent or drug to the substrate and/or the release rate of the immobilized active agent or drug from the substrate in a given bio-fluid or tissue environment when administered to an individual. These capping agents may form a layer on the substrate surface to modify the affinity of the compound or drug for the substrate, restrain the release of the active agent or drug from the substrate and/or modulate or alter the quantity and quality of interactions between the active agent or drug and the substrate during solvent evaporation. Without being bound by any theory, apart from modifying or altering interactions between the active agent/drug and substrate, restrained release of the active agent or drug due to the presence capping agent may also be caused by "trapping" the compound/drug to the interior pores of the substrate and/or impeding or restraining access of a bio-fluid to the interior pores of the substrate to liberate the active agent or drug. The capping agents will eventually become dissolved or possibly digested when the formulation is administered to an individual such that the capping agent is no longer bound to the substrate. As a result, its effects on the release rate of the active agent or drug are removed upon its disassociation from the substrate. Selection of the capping agent(s) may be based on its chemical groups that may non-covalently bind or interact with the compound or drug of interest as well as the immobilizing substrate.

According to embodiments of the present invention, the capping agent(s) may include compounds like magnesium stearate (Mg stearate), steric acid, stearyl fumarate (multiple salt forms) and other compounds, and combinations thereof. These so-called "capping" agents or compounds may include those that have been used as standard lubricants for optimal tablet formation by direct compression and are known to be safe. For example, in Example 1 below, Mg stearate is used as a hydrophobic capping agent for use with Liothyronine immobilized to a cellulose excipient. The Mg stearate in this formulation also provides a lubricant function to promote the formation of uniform tablets. Many of these capping agents, such as magnesium stearate or stearic acid, are known to be hydrophobic, while others, such as stearyl fumarate, are more hydrophilic. Accordingly, these capping agents or lubricants may be used either alone or in combination (e.g., Mg stearate and stearyl fumarate or stearic acid) to further modulate control of drug or compound release from the excipient or substrate. For example, combinations of capping agents or lubricants having competing characteristics (e.g., hydrophobic versus hydrophilic) may be added in relative amounts to tailor or fine tune the stability and/or release properties of the compound or drug from the formulation.

According to some embodiments, capping agents may also include polymers, such as polypeptides, etc. According to some embodiments, a polypeptide may be used as a capping agent to control the release properties of the formulation, such as the timing and/or physiologic environment in which the active agent or drug is released following administration. Amino acids that are part of a polypeptide chain can have pKa values determining how the certain substituents or R-groups change in response to pH. For example, as described in Example 10 below, poly-glutamic acid may be used as a capping agent to regulate pH-dependent release of prednisone in the small intestine (pH=6.5) rather than in the stomach (pH=1.0). Since the pKa value for poly-glutamic acid (poly-Glu) is about 4.5, transport of the poly-Glu from the stomach to the small intestine causes the carboxyl group to be converted from the —COOH to the —COO$^-$ form, which results in the capping agent dissolution and release of the active agent or drug (i.e., prednisone) into the lumen of the small intestine to be further transported into the blood to act as an anti-inflammatory agent in target tissues.

According to embodiments of the present invention, the binding affinity may be designed for a given active agent by choosing the substrate empirically or based on predicted interactions. Some general principles may be used to predict binding affinity. For example, activated carbon is highly porous and has a high affinity for hydrophobic compounds, whereas silica has an affinity for more hydrophilic compounds. Although the strength of affinity between a given substrate and active agent/drug may be difficult or confounding to predict in many circumstances (especially those with a variety of hydrophilic chemical groups presented on their surface), binding affinity and release properties may still be determined by empirical observation using known protocols and techniques (e.g., by HPLC analysis over a period of time). Thus, a continuum or spectrum of binding affinities may be engineered for a given active agent or drug. In addition, depending on the identity of the active agent or drug, a combination of substrates may be used together to create two different binding affinities in the same formulation. This may be useful in creating different phases of release of the active agent or drug from a formulation when administered to an individual. Portions of the active agent or drug bound to a lower affinity substrate would be released more rapidly (and over a shorter time frame) than portions of the active agent or drug bound to a higher affinity substrate in the same formulation.

Release properties may also engineered by the degree of porosity and surface area per unit of mass of a given substrate. An active agent or drug bound to interior pore surfaces of a substrate having a higher porosity and surface area per unit of mass will generally be released more slowly due to more limited diffusion into the bio-fluid. Moreover, the release properties of an active agent or drug from a substrate may also be modified or altered by using capping agents that may be pre-immobilized or co-immobilized with the active agent or drug to the substrate and/or subsequently immobilized to the substrate after the active agent or drug is bound to the substrate. Thus, the release properties of an active agent or drug from a drug formulation or dosage form may be engineered by the selection of substrate affinity and/or substrate porosity or surface area as well as by using other modifying excipient(s) and capping agent(s).

Thyroid hormones present an attractive candidate for use with the present invention due in part to challenges and difficulties in achieving euthyroid targeted dosing, small amounts of these drugs per dosage unit, and the instability of these drugs in storage. Different individuals also have varying sensitivities to thyroid hormones that must be managed carefully by a health care provider. Both triiodothyronine (T3) and thyroxine (T4) are each hydrophobic in nature due to the presence of iodines and are thus suitable for use in organic solvents. Typically, anhydrous solvents are preferred for the dispersed immobilization of thyroid hormones to a substrate because even a small presence of water in thyroid hormone drug formulations can cause degradation of these drugs in storage. In general, due to the small amount of thyroid drug in a large volume of excipients in the final formulation used to in making the dosage form of the final drug product (e.g., tablets), a master mix that has a higher concentration of the thyroid drug(s) will typically be prepared first (in a smaller volume) that may then be diluted to a desired concentration by mixing or blending with additional excipients.

Many active agents or drugs may be produced and/or exist as liquids or oils at room temperature. Currently, it is challenging to mix these liquid or oily preparations with powder excipients (especially in small amounts) and achieve even distribution of the active agent or drug throughout the powder formulation. Adding the liquid to the excipient powder will often result in the formulation becoming lumpy and unevenly mixed, and the powder formulation may not flow through equipment well. Utilizing longer blending and mixing times to overcome this issue would slow down production and increase costs. Thus, these liquid or oily active agents or drugs may often be placed into gel caps or other gel delivery systems (instead of tablets) for oral administration. For example, many hydrophobic agents, drugs or nutrients, such as vitamin E and omega-3 fatty acids, are made into gel cap dosage forms.

Embodiments of the present invention overcome these challenges in formulating these liquid or oily agents/drugs into solid dosage forms, such as powders and tablets, by allowing these liquid or oily agent/drug to be solubilized into a solvent of choice and then evenly distributing and immobilizing the active agent/drug to the substrate. Thus, embodiments of the present invention may be used to place these active agents or drugs into solid dosage forms, such as powders and tablets, instead of gel caps. By first distributing the agent/drug in solution and then immobilizing the agent/drug in a highly distributed fashion, the prior issues with dispersing and tableting these agents/drugs may be overcome.

According to embodiments of the present invention, methods are provided for preparing improved formulations comprising an active agent or drug. In a first step, a volume of a solvent(s) of choice may be added to a container, such as a round bottom flask. One or more active agent(s) or drug(s) that are to be immobilized to a substrate may then be added to the solvent in the container to dissolve the active agent(s) or drug(s) into the solvent. It is generally more practical to add the active agent(s) or drug(s) to the solvent already present in the container although either order of addition is theoretically possible. Although two or more solvents may be used with two or more active agents or drugs having different solubilities, it may generally be preferred that the two or more active agents or drugs are dissolved in the same solvent if possible. Optionally, the solvent may then be adjusted or neutralized to a desired pH by addition of an acid or base. The solvent containing the one or more active agent(s) or drug(s) may be mixed or agitated, such as by using a magnetic stir bar in the container, at a desired temperature, such as room temperature or at an elevated temperature below the boiling point of the solvent, until the active agent is mostly or fully dissolved in the solvent.

The active agent(s) or drug(s) may be determined to be dissolved and in solution when the solution becomes clear by visual inspection. It is important that most or all of the active agent(s) or drug(s) be in solution so it is generally preferred that the substrate(s) is not added until after the active agent(s) or drug(s) are in solution because the addition of the substrate(s) may interfere with the dissolution of the active agent(s) or drug(s) and the visual inspection of the dissolving step. After the active agent is in solution, an amount of one or more substrate(s) may then be added to the solution. With the addition of the substrate(s), the solution may turn into a slurry or suspension especially if the substrate(s) is not soluble in the solution. One or more other ingredient(s) or excipient(s) that may be generally recognized as safe (GRAS) may also be optionally added to the solution, such as one or more lubricant(s) or capping agent(s), which may also become immobilized to the substrate(s) in a subsequent evaporation and immobilization step. These additional excipient(s), including any capping agent(s), may be added to the solvent with the active agent(s) or drug(s) prior to the active agent(s) or drug(s) being dissolved, or they may be added to the solution after the active agent(s) or drug(s) are dissolved either before, with or after the addition of the one or more substrate(s) to the solution.

After the active agent(s) or drug(s) are dissolved and the substrate(s) are added to the solution (with or without any additional ingredients or capping agents), the solvent(s) may be evaporated under a reduced pressure or vacuum (e.g., about 30 inches of Hg or less) until an odorless, free-flowing powder of mainly the substrate is formed. Formation of the free-flowing powder will generally be observable by visual inspection. This step may take a short period of time, such as about several minutes to about a half-hour. As a result, the resulting substrate powder formed should contain the active agent or drug immobilized or bound to the substrate surface. For purposes of the present invention, the term "substrate powder" refers to a powder of a substrate(s) with one or more active agent(s), drug(s), excipient(s), and/or capping agent(s) immobilized, bound, etc., to the substrate(s) as a result of a dissolution and evaporation process of the present invention. This evaporation step may also be performed at an elevated temperature to encourage evaporation and removal of the solvent(s). For purposes of the present invention, the term "elevated temperature" means any temperature above room temperature or greater than 20° C. or 25° C. For example, the elevated temperature may be selected to be at or below the boiling point of the solvent at standard conditions (e.g., at or within about 5° C. below the boiling point). The elevated temperature may generally be chosen to avoid "bumping" of the suspension caused by localized boiling that is too rapid. Excessive bumping may also be avoided by addition of an inert boiling stone during the solvent evaporation process.

As an alternative to adding an additional active agent(s) or drug(s) to the first solution with the first solvent(s), the free-flowing substrate powder having the immobilized active agent(s) or drug(s) from the first immobilization and evaporation step may be added to a second solution with a second solvent having the additional active agent(s) or drug(s) dissolved therein, and the second solvent may then be evaporated to form a second substrate powder with the two or more active agents or drugs immobilized thereto. In other words, multiple active agent(s) or drug(s) may be immobilized, bound etc., to the substrate(s) in subsequent and sequential rounds of solvent dissolution and evaporation. The second solvent may be the same or different than the first solvent although the second solvent may preferably be different to avoid re-suspending or re-dissolving the active agent(s) or drug(s) immobilized in the first set of steps in the second solvent. As another alternative, a substrate powder having an active agent(s) or drug(s) immobilized to it from a previous step may be mixed or blended with a second active agent(s) or drug(s) that is not immobilized to a substrate (see, e.g., Example 6 below).

Similarly, any additional excipient(s) or capping agent(s) may be immobilized onto the substrate(s) through a subsequent and sequential dissolution and immobilization step(s). The free-flowing substrate powder having the immobilized active agent(s) or drug(s) from the first immobilization and evaporation step may be added to a second solution with a second solvent having the additional excipient(s) or capping agent(s) dissolved therein, and the second solvent may then be evaporated to form a second substrate powder with the active agents or drugs and the additional excipient(s) or capping agent(s) immobilized thereto. The second solvent may be the same or different than the first solvent although the second solvent may preferably be different to avoid re-suspending or re-dissolving the active agent(s) or drug(s) immobilized in the first set of steps. The reverse order is also possible. An excipient(s) or capping agent(s) may be dissolved in a first solvent, which is evaporated to form a substrate powder with the excipient(s) or capping agent(s) immobilized, bound, etc., to the substrate(s). This substrate powder may then be added to a second solution with a second solvent having one or more active agent(s) or drug(s) dissolved therein, which is evaporated to form a second substrate powder with the active agent(s) or drug(s) as well as the excipient(s) or capping agent(s) immobilized, bound, etc., to the substrate(s).

After a free-flowing substrate powder is formed containing the active agent or drug immobilized to the substrate by evaporation of the solvent(s) according to any of the above methods, the atmosphere surrounding the substrate powder may be replaced with an inert gas, such as argon, nitrogen, xenon, etc. Prior to replacement with the inert gas, any atmosphere may be first removed by reduced pressure or vacuum (if not already removed during the evaporation step. This inert gas replacement step may take place almost instantaneously and immediately (e.g., less than about 1-2 minutes). The steps of vacuum or reduced pressure removal of gas and replacement with an inert gas may be repeated one or more times (e.g., a total of 2-4 rounds of vacuum and gas replacement). The substrate powder may optionally be combined with other ingredient(s) or excipient(s) that may commonly be used in pharmaceutical formulations, such as the excipients listed above.

After the powder is formed (with or without any additional excipients or ingredients) and the atmosphere has been optionally replaced with an inert gas, the resulting formulation or substrate powder may then be optionally formed into a desired dosage form, such as by compression into tablets. The resulting formulation or dosage form may then be stored in air-tight vials or containers, which may contain an inert gas, for storage. The substrate powder may also be placed into air-tight vials or containers following inert gas replacement without the addition of other excipients to the substrate powder. The timing of the steps for removal and replacement of the atmosphere with an inert gas may be done after the substrate powder is formed or after the substrate powder is combined with any additional excipients to form a final formulation. Equipment used in the blending (e.g., cone blender) and dosage formation (e.g., tablet compression machine) processes may be enclosed and capable of maintaining a reduced or vacuum pressure and/or allowing the replacement or infusion of an inert gas such that air or other contaminants are not allowed to infiltrate the formulation during manufacturing following formation of the substrate powder. Indeed, the blending and dosage forming equipment may be part of an integral system that is jointly enclosed such that air does not contact the formulation between the blending and dosage forming processes. Thus, the inert gas replacement step may be done during the blending and/or dosage forming steps.

According to some embodiments of the present invention as introduced above, a substrate(s) may be dissolved in a dispersing solvent along with an active agent(s) or drug(s) (instead of forming a suspension or slurry of the insoluble substrate(s) in the solution). In these cases, the substrate would include those that are soluble in the dispersing solvent, such as polyethylene glycol (PEG), gelatin or collagen, as well as other polysaccharides and polypeptides, and potentially many others. To form a substrate powder of the present invention, the dispersing solvent may then be evaporated as described above (perhaps at an elevated temperature). As the solvent evaporates and the volume of solution decreases, the substrate(s) and the active agent(s) or drugs(s) may begin to fall out of solution, precipitate and eventually form a substrate powder when the solvent is removed. With many polymer substrates, such as polypeptides, in solution with an active agent or drug, precipitation of the substrate may cause it to undergo tertiary folding (especially if the solution is heated to extend the structure of polymer substrate in solution) to entrain, entrap or contain the active agent or drug in the interior of the folded polymer of the substrate powder. Excipients or capping agents other than the substrate(s) may be co-precipitated by these methods.

As another (analogous) alternative to forming a substrate powder of the present invention with the active agent(s) or drug(s) bound to it, a solution of a dispersing solvent containing the substrate(s) and active agent(s) or drug(s) may instead be co-precipitated out of solution by addition of a precipitating solvent (see, e.g., Examples 11 and 12 below). The precipitating solvent may include organic solvents especially if the solvent dissolving the active agent(s) or drug(s) and substrate(s) is an aqueous solvent. The dispersing and precipitating solvents will generally be a miscible solvent pair, the solvent pair defined as including a precipitating solvent that are known or determined empirically to cause or trigger co-precipitation of the substrate(s) and active agent(s) or drug(s) dissolved in the dispersing solvent when added to the dispersing solvent. According to some embodiments, the precipitating solvent may include one or more of: acetone, hexane, tetrahydrofuran (THF), triethyl amine, diethyl amine, butyl amine, propyl amine, trifluoroacetic acid (TFA), isopropyl alcohol, ethanol, 2,2,2-trifluoroethanol, methanol, acetonitrile, dioxane, perfluorohexane, and many others. Precipitation by this method may also serve to entrain, entrap or contain the active agent or drug within the interior of the folded polymer substrate. Excipients or capping agents other than the substrate(s) may be co-precipitated by these methods.

Thus, either the evaporation approach or the precipitation by addition of a precipitating solvent approach may be chosen in circumstances where both the substrate and active agent/drug are dissolved in solution. Indeed, any method described herein in which a substrate powder is formed by evaporation (e.g., by vacuum or reduced pressure) may potentially be replaced with precipitation by addition of a precipitating solvent if the substrate(s) and active agent(s) or drug(s) are dissolved in the dispersing solvent. Following precipitation of the substrate with the immobilized active agent/drug, the precipitate may then be dried into a substrate powder by evaporation of the solvents (e.g., by reduced or vacuum pressure). Alternatively, the precipitate may be allowed to settle or pelleted by centrifugation, and the excess solvents aspirated and the remaining precipitate may then be lyophilized or dried by evaporation into a substrate powder. Either method of preparing a substrate powder may be followed by vacuum removal and replacement with an inert gas.

According to another aspect of the present invention, compositions are provided that are made according to any of the methods of the present invention. Such compositions may comprise one or more active agent(s) or drug(s) immobilized, bound, etc., to one or more excipient substrate(s), which may be in the form of a powder, such as a substrate powder, or dosage form as described above. The active agents or drugs may include a wide variety of drugs and may be formulated, blended, combined, etc., with one or more excipient(s) as described above. Thus, compositions of the present invention include pharmaceutical compositions in the form of powders, formulations, dosage forms, etc., that comprise the substrate powder possibly in combination with one or more other pharmaceutically acceptable and suitable excipients, such as one or more of the excipients mentioned above. The composition may further comprise one or more capping agent(s), which may modify or alter the release properties of the active agent or drug from the composition when administered, such as by modifying or altering the affinity between the active agent/drug and the substrate and/or by limiting the diffusion rate of the active agent/drug from the substrate as well as the accessibility of the active agent/drug by a bio-fluid. Compositions of the present invention may have improved stability of the active agent or drug and longer shelf life in storage in comparison to existing compositions of the same active agent or drug. Compositions of the present invention may also have extended release properties of the active agent or drug in comparison to existing compositions of the same active agent or drug when administered to an individual as described further herein and as measured according to established techniques in vitro (see, e.g., Examples 1 and 2 below).

The amount of active agent or drug in compositions of the present invention and the ratio of active agent or drug to the amount of substrate(s) and/or other excipient(s) will depend on the final formulation intended for use such as the final amounts and ratios of amounts of the active agent or drug in the final formulation, dosage form or drug product. A person skilled in the art would be able to calculate the amounts that may be used in forming a substrate powder of the present invention as well as how much of the substrate powder with the immobilized active agent or drug should be added to other excipient(s) to make a final product or formulation having the desired amount and concentration of active agent or drug.

According to another broad aspect of the present invention, compositions made according to the methods of the present invention as described herein may be administered to an individual. Since the present methods are generally directed to immobilizing an active agent or drug to a substrate powder, compositions administered according to methods of the present invention may generally be solid dosage forms administered orally. However, given the higher stability of active agents or drugs in present powder formulations, substrate powders may be reformulated from storage into other dosage forms for administration to an individual. For purposes of the present invention, an "individual" refers generally to a mammal and more preferably to a human that may be receiving medical care or treatment as a patient. The term "individual" may also refer to non-human mammals, such as dogs or other pets or agricultural animals, for veterinary applications.

Because substrate powders of the present invention may generally provide for a more extended release rate of an active agent or drug, compositions of the present invention comprising, or formulated with, these substrate powders may be administered less frequently perhaps at a higher unit dosage. Many drugs are difficult to maintain at consistent and desired levels in the body especially with fewer doses administered per day. Such drugs may be highly active and thus cause a spike in activity following administration. More extended release dosage forms may provide a way to achieve consistent levels of the drug that avoid spikes or fluctuations in activity. Compositions and formulation methods of the present invention provide a way to achieve extended release of an active agent or drug. The more extended and even release of an active agent or drug from formulations, dosage forms and drug products of the present invention following their administration to an individual may allow for more precise dosing of these drugs and fewer doses to be given per day.

Thyroid hormones provide a good candidate for use with methods and compositions of the present invention for reasons stated above. Currently, persons experiencing hypothyroidism or myxedema may be treated with drugs comprising replacement doses of triiodothyronine (T3), levothyroxine (T4) or a combination of the two to maintain a euthyroid condition. Currently, T4 drugs (e.g., Synthroid®, Abbott) dominate the marketplace with T3 drug products (e.g., Cytomel®, Pfizer) filling in significant but only niche portions of the market.

The thyroid hormones, T3 and T4, are produced by the thyroid gland primarily to regulate bodily metabolism as well as other physiologic processes. Although T4 is produced in much higher amounts initially than T3, T3 has a much more potent activity than T4, and T4 is converted into T3 in peripheral tissues. Thus, it may seem that replacement therapy with T3 would be effective since T3 is more active than T4 and T4 is converted into T3 in the body. However, the high activity of T3 and its much shorter half life in the blood (i.e., about 20-30 hours) following administration have made replacement therapies with T3 alone problematic. If overdosed, T3 can cause side effects and toxicity. Even if appropriately dosed, treatment with T3 (even when administered multiple times per day—e.g., three times per day according to standard protocols) can cause spikes in activity and uneven effects. Thus, current standard therapy for hypothyroidism typically consists of administering T4 to the patient, which has a much longer half life in the blood (i.e., greater than 7 days) and can be administered once a day with the T4 being converted into the more active T3 in the body.

The current view of thyroid hormone replacement therapy is that blood levels of thyroid hormones (particularly T3) correlate with the downstream physiologic effects of these drugs. Accordingly, current treatment protocols typically include either once a day dosing with T4 or 3-4 doses per day of T3 (due to the shorter half-life and higher activity of T3) to maintain consistent blood levels of these drugs. Given that formulations of the present invention have a more extended time release of drugs immobilized to an excipient substrate, it is presently proposed that a formulation or dosage form of the present invention having T3 immobilized to a substrate would have more extended release of T3 and may thus be administered less frequently than standard protocols requiring multiple doses per day. Indeed, it is found that present formulations with T3 do result in more extended release of this drug from the excipient substrate with long lasting effects when administered to an individual. Due to the more extended release of the drug, present formulations of T3 are found to have a half-life that may exceed several days (i.e., more than 70 hours) following administration.

According to embodiments of the present invention, it is found that once a day dosing of a present formulation of T3 may be used to maintain a euthyroid state in patients. Contrary to the current and traditional view, it is surprisingly found that administration of a present formulation and dosage form of T3 maintains a euthyroid state as determined by clinical presentation and measurement of levels of downstream target gene products despite a decline in thyroid hormone levels in the blood. For example, levels of thyroid stimulating hormone (TSH) are reduced or inhibited by thyroid hormones through a negative feedback, whereas levels of other target gene products, such as transferrin and sex hormone binding globulin (SHBG), are increased in response to thyroid hormone treatment to euthyroid levels. As shown in example 7 below and FIG. 3, levels of TSH decrease and remain low following a single dose of a present formulation of T3 (given to normal healthy adults) long after blood levels of T3 decline.

As further shown in Example 8 below and FIG. 4, patients receiving standard treatment of levothyroxine for treatment of hypothyroidism that were switched to once a day dosing of a present formulation of T3 for six weeks maintained a euthyroid state as measured by clinical presentation and measurement of blood levels of downstream targets of T3 in these patients. Following the switch to treatment with the present formulation of T3, levels of TSH remained low (actually decreased further), and levels of SHBG and transferrin remained elevated (if not increased slightly). Thus, treatment with present formulations comprising T3 immobilized to a substrate (e.g., once a day dosage of present formulations of T3) provides an effective alternative to present treatment protocols for individuals having, experiencing, or suffering from hypothyroidism, myxedema or myxedema coma.

Based on present findings that downstream euthyroid effects continue to occur after a decline in the amount of thyroid hormone in the blood (and contrary to current views in the field), amounts of T3/T4 present in the blood may not be the best indicator of present physiological activity and effects of thyroid hormones following treatment. Instead, it is proposed that the blood may only be an intermediary compartment for the activity of T4 and/or T3 in peripheral tissues. Without being bound by any theory, it is believed that following administration of present formulations of T3, for example, the T3 becomes redistributed or partitioned in peripheral tissues (e.g., in fat tissue or bound to cell surface receptors) where it may remain active after its decline in the blood.

Therefore, based on this new paradigm of belief that it is the levels of thyroid hormone (e.g., T3) in peripheral tissues that determines present effects of T3/T4 (rather than blood levels of these hormones), and given the more extended release of T3 from present formulations, it is presently proposed that once a day dosing of present compositions of T3 may be used to treat hypothyroidism or myxedema in contrast to existing treatment protocols with T3. It is further believed that in addition to T3-immobilized substrate containing compositions, present formulations comprising bound T4 (or combined T3 and T4) may also be used with the present technology to provide extended release of these drugs as well as to overcome instability the issues for T4 in storage. Compositions of the present invention comprising T4 may comprise an amount per dosage of about 50 to about 200 µg of T4, or about 100 µg of T4. A composition comprising both T3 and T4 may generally have an amount of each of these drugs that is a fraction of the amounts used when they are administered alone.

According to embodiments of the present invention, a treatment protocol is proposed comprising once a day dosing of a pharmaceutical composition of the present invention comprising T3 and/or T4 immobilized to a substrate. For example, such a method may comprise administering a dosage of a formulation of the present invention including an amount per dosage of T3 in a range from about 10 µg to about 50 µg of T3 once per day (e.g., about 20-40 µg T3 once a day or about 30 µg T3 once a day). According to some embodiments, a single daily dose of about 15 µg T3 may be administered for a period of time (e.g., for about 1-3 weeks or about 2 weeks) to establish tolerance for the drug, followed by administering a higher dose that matches the normal production rate more closely (e.g., about 20-40 µg T3 once a day or about 30 µg T3 once a day). This is contrary to present belief in the field that once a day dosing of T3 cannot be used as an effective and efficacious approach to treatment of hypothyroidism in patients.

By overcoming the perceived shortcomings of T3 replacement therapy, other benefits may be achieved. One issue with T4 therapy is that it is not as well absorbed into the blood from the digestive tract as compared to T3. With oral administration, T3 has a higher bioavailability (e.g., greater than about 95%) than T4 (e.g., about 45-65%). The lower and variable absorption of T4 into the blood from the gut also poses challenges to certain and predicable dosing of individuals. Thus, an advantage of T3 therapy is that the dosing is more predictable. Most or all of the T3 will release from the present formulations and products when administered, albeit in a more extended fashion than straight formulations. Another advantage of T3 replacement therapy over T4 is that it overcomes the issue that some individuals have in not being able to sufficiently convert T4 into T3 in the body.

Daily dosing may then be adjusted depending on clinical presentation of the patient as well as measurement of downstream targets and indicators of thyroid hormone activity in samples from the patient, such as levels of TSH, SHBG and transferring (to name a few). In fact, it is proposed based on present findings that thyroid hormone activity in peripheral tissues is maintained after a decline in hormone levels in the blood, that present methods comprising monitoring and/or determining the levels of gene products that are affected by T3/T4 activity (i.e., downstream targets, indicators, markers and/or effectors of T3/T4 activity) may provide a better measure and basis (along with clinical presentation) for adjusting T3 and/or T4 dosing levels given the lesser importance of levels of T3 and/or T4 in the blood. Thus, one or more tissue samples or biopsies, such as blood, may be taken from the individual over time during treatment to assess or measure one or more of these downstream targets, etc., of T3 and/or T4. Following measurement of one or more of these downstream indicators of thyroid hormone activity (e.g., according to any known assay for measuring levels of mRNA or protein of thyroid hormone gene targets, such as by Northern or Western blotting, use of array analysis, gene chips, enzyme-linked immunosorbent assay (ELISA), etc.) after and/or during treatment, the dosage amount of the active agent or drug (e.g., T3 and/or T4) may be adjusted accordingly for a given patient to maintain these levels within euthyroid ranges.

Although much of the description of the present invention is directed to pharmaceutical compositions and immobilizing active agents or drugs to a substrate, it is also envisioned that embodiments of the present invention may be used to immobilize or bind a reactant or catalyst that may be added to a reaction mixture for stability of the reactant or catalyst and/or slow-release of the reactant or catalyst into the reaction, such as to delay or control the rate and timing of completion of the reaction. In these embodiments, the substrate will preferably be inert in the reaction. For example as provided in Example 9 below, controlled pore glass may be used as a substrate to bind glycouril for use in a protein iodination reaction.

EXAMPLES

Example 1

Formulation and Tableting of Liothyronine (T3)

A magnetic stir bar is placed in a 100 ml round bottom flask. About 50 ml of tetrahydrofuran (having less than 0.05% water) is placed in the flask at room ambient temperature. About 8.5 mg of Liothyronine, sodium (3,5,3'-Triiodo-L-Thyronine, mono sodium salt), is added, and the solvent is neutralized with about 0.1 ml of 1.0 N HCl in water. The solution is mixed until all of the Liothyronine is visibly dissolved, and Liothyronine concentrations are verified spectrophotometrically. About 25 grams of cellulose powder (e.g., Avicel® 112) and about 0.5 grams of Mg Stearate are added to the solution. Since volatiles are removed in this procedure, "loss on drying" values are taken into account in all component measurements to ensure precise final dosing. The tetrahydrofuran solution is removed by vacuum evaporation in a 60° C. bath until the slurry or suspension containing the cellulose and Liothyronine is converted to a free-flowing powder. Then, the vacuum is replaced with argon gas. A vacuum is reestablished and again replaced with argon gas to obtain a free-flowing, odorless powder that may be suitable as a complete formulation for tableting. Tablets (e.g., containing 150 mg±5 mg) can be formed by direct compression to a hardness of about 10 to 12 kPa. According to this example, these tablets contain about 50 µg±2 µg of Liothyronine. The tablets may be stored in air-tight containers under argon.

Example 2

Dissolution and Sustained Release of Liothyronine Formulations

The dissolution rate and release of Liothyronine from the product of Example 1 is measured and compared to Cytomel® (50 µg Liothyronine dose) using a Type 3 apparatus as described in U.S. Pharmacopeia (USP) Monograph 34:3317. Sustained release of Liothyronine from the tablets made in Example 1 is demonstrated. As shown in the table of FIG. 1, a maximum solution concentration of Liothyronine released from the tablets of Example 1 was observed at 270 minutes. In contrast, maximum concentration of Liothyronine from Cytomel® was observed at 40 minutes, and there is about 30% loss of concentration of Liothyronine from Cytomel® after about 120 minutes. As further shown in FIG. 2, the Liothyronine was released more slowly from the tablets of Example 1 and reached a peak concentration later in solution in comparison to Cytomel®. Thus, the Liothyronine product made according to Example 1 has extended release properties.

Example 3

Stability of Liothyronine (T3) in Tablets

The product of Example 1 was stored in tightly capped PET bottles purged with dry argon and stored under accelerated stability testing conditions (40° C., 75% relative humidity) as described in FDA Guidance Q1A(R2) for Stability Testing of New Drug Substances and Products. In these experiments, no statistically significant loss of Liothyronine was observed in the tablets of Example 1 during the first 13 months of testing in 3 standard production lots. Thus, the Liothyronine product formed in Example 1 is stable enough in storage over a reasonable period of time for distribution.

Example 4

Dry Blending of Primary Immobilization Substrate Powder

Levothyroxine, sodium, pentahydrate (e.g., 18.6 mg) was dissolved in about 50 ml of THF and neutralized by the addition of 1.1 ml of 1.0 N HCl in water. Similarly to Example 1, the solution is mixed until dissolution of all solids is observed. Avicel® 112 (e.g., 25 grams) and Mg Stearate (e.g., 0.5 grams) are added and mixed, and the procedure is continued as described in Example 1 to form a free-flowing powder. This powder was further blended in the dry state with an additional 225 g of microcrystalline cellulose and 4.5 g Mg Stearate in a double-cone blender for 4 minutes at 1 revolution per second or until homogeneous. About 150 mg tablets may be formed by direct compression of the product formed by this method. The resulting tablets contain about 10 mcg of anhydrous L-thyroxine as calculated and measured by HPLC under the conditions described in the USP Monograph 34:3317.

Example 5

Formulation with Combined Drugs

Multiple drugs that are co-soluble in a solvent of choice may be combined in the solvent. Thus, a combination of Liothyronine, sodium (e.g., 8.5 mg) and Levothyroxine, sodium (e.g., 85.0 mg) are both dissolved in about 50 ml of THF and neutralized by the addition of 1.1 ml of 1.0 N HCl in water. Similarly to Example 1, the solution is mixed until dissolution of all solids is observed. Avicel® 112 (e.g., 25 grams) and Mg Stearate (e.g., 0.5 grams) are added and mixed, and the procedure is continued as in Example 1. About 150 mg tablets may be formed by direct compression of the product formed by this method. The resulting tablets contain a 1.8 to 1 ratio of anhydrous L-thyroxine (e.g., 91.4 µg) to L-Triiodothyronine (e.g., 50 µg) as measured by HPLC under the conditions described in the USP Monograph 34:3317.

Example 6

Primary Coating Followed by Secondary Blending for Multiple Drugs

Example 4 provides a scenario where two or more drugs are combined in the solvent and immobilized together onto the excipient substrate. To achieve a differential release rate among multiple drugs from the same dosage form (e.g., a tablet), one drug may be applied as a substrate carrier coating (i.e., immobilized to the substrate) similarly to Example 1. Once the powder containing the first drug immobilized to the substrate is formed by this process, it may then be subsequently blended with a powder containing a second drug. Accordingly, the first drug would be immobilized to the excipient/substrate, whereas the second drug would be free and not immobilized to any substrate in the mixture. Once this combined formulation is adequately mixed, it may be made into tablets by direct compression.

As an example of this approach, about 85,000 units of Vitamin D3 is dissolved in about 50 ml tetrahydrofuran solvent as similarly described in Example 1. Then about 10.0 grams of Calcium Carbonate, about 15 grams of microcrystalline cellulose, and about 0.5 grams of Calcium Stearate are added to the solvent. Vacuum removal of the solvent and replacement of with argon yields a blended, formulated powder suitable for tableting by direct compression, which may be used as a stable oral dosage form for the treatment of Calcium deficiencies. The Vitamin D3 will be immobilized to the cellulose substrate, whereas the calcium carbonate will not be bound to the substrate.

Example 7

Sustained Effects of Oral Liothyronine

The product utilized in this trial was prepared as described in Example 1 to contain 50 mcg Liothyronine and was given as a single oral dosage source of Liothyronine as described in the FDA Guidance on Liothyronine Sodium. Active Ingredient: Liothyronine Sodium; Form/Route: Tablets/Oral; Recommended Studies: 1 Study; Type of study: Fasting; Design: Single Dose, in vivo; Dose and strength: 100 µg (2×50 µg); Subjects: Normal healthy male General Population; Measurements in Plasma: Total (free+bound) Liothyronine and thyroid-stimulating hormone (TSH). Baseline levels of Liothyronine and TSH were measured at 1 hour pre-dose (−1.0 hour). The mean of the three pre-dose samples were subtracted from each measured post-dose concentration.

These studies show safety and efficacy of the Liothyronine product of the present invention, as well as a sustained effect profile compared to values presented in the extensive pharmacokinetic (PK) literature on Cytomel® and other similar formulations containing Liothyronine. In particular, T3 levels in the blood following the single 100 mcg dose, peaked as T3 passes from the digestive system into the blood. However, the decline in blood levels of T3 is believed to be due to re-distribution from the intermediate blood compartment to the target tissues, not due to metabolic removal from the system, as evidenced by the prolonged effects of the hormone (lower TSH levels) after its decline in the blood (see, e.g. FIG. 3). Importantly, TSH levels remain suppressed for over 72 hours, long after T3 blood levels have declined to base line, demonstrating a long acting effect of the Liothyronine oral therapy from Example 1 of this invention. This result allows for once per day dosing for maintenance of the euthyroid state due to the sustained release and presence of the drug in target tissues.

Example 8

Clinical Use of Sustained Release Liothyronine

The present cross-over study utilized hypothyroid patients, selected on the basis of their current treatment with Levothyroxine (T4). The patients were switched from T4 to a single daily dose 15 micrograms of T3 prepared as described in Example 1 for two weeks (to show tolerance), followed by 30 micrograms of the composition of Example 1 for an additional 4 weeks (i.e., a total of 42 days), and then switched back to their original Levothyroxine (T4) dose. Blood samples were taken before dosing and assayed weekly for Total T3, T3 Uptake, Total T4, Free Thyroxine Index, and TSH. Blood levels of Ferritin and SHBG were also measured as additional known thyroid-hormone regulated gene products. As shown in FIG. 4, once a day dosing of 30 mcg of T3 in tablets prepared as described in Example 1 maintains the euthyroid condition despite the decline in T4 following the switch from Levothyroxine treatment.

As expected, Total T4 decreases in the absence of a Levothyroxine dosing source in these patients. It was also found that levels of TSH remained low within the euthyroid range (see reference range) in these patients over the six-week period, whereas levels of Ferritin and SHBG remained elevated within the euthyroid range (see reference ranges)

over the same period despite the decline in T4. Patients also reported feeling healthy during the cross over study period.

Example 9

Coating Controlled pore Glass with Glycouril

Alternate substrates can be utilized to achieve specific advantages. For example, the siloxyl groups of controlled pore glass can provide differentiated binding properties and a very large surface area due to the high porosity of the etched glass. In addition, protracted diffusion from this highly porous substrate provides an additional mechanism for sustained release. Controlled pore glass may be prepared according to known methods, such as the method described in Haller, W., U.S. Pat. No. 3,549,524, the entire contents and disclosure of which is hereby incorporated by reference. As an example, the controlled pore glass may be prepared with 2000 angstrom nominal pore size and super fine particle size and used as a substrate. About mg of Glycouril (1,3,4,6-Tetrachloro-3a-6a-diphenylglycouril) was dissolved in about 50 ml of methylene chloride in a 100 ml round bottom flask, and about 10 grams of controlled pore glass was added and mixed to form a uniform suspension. The slurry was vacuum evaporated in a 40° C. water bath and then dried under vacuum for about 18 hours.

Example 10 pH-Dependent Delivery of Prednisone

Prednisone (0.830 g) is dissolved in 100 ml anhydrous ethanol and microcrystalline cellulose (25 g) and Mg searate (0.5 g) are added with mixing. The slurry was dried to a substrate powder similarly to Example 1, and a second solution containing 0.5 g Poly-L-Glutamic acid in 5 ml water/45 ml THF was added and again dried to a substrate powder under vacuum. The product was formed into 150 mg tablets by direct compression for use as an oral dosage form containing about 5 mg prednisone per tablet.

Example 11

Immobilization of Prostaglandin E1 to PEG for Oral Delivery

Poly Ethylene Glycol (10 gm, PEG 6000, polydisperse) was dissolved in hot methanol (50 ml), and Prostaglandin $E_1$ (32 mg, $PGE_1$, misoprostol) was added and dissolved with stirring to form a clear solution. The PEG and $PGE_1$ were then co-precipitated by the rapid addition of isopropyl alcohol (100 ml). Microcrystalline cellulose (10 gm) and Mg Stearate (0.5 gm) were added to the suspension and mixed and the solids were isolated by removal of the solvent under vacuum. The resulting powder is suitable for further formulation or tableting by direct compression. Tablets containing about 100 mcg $PGE_1$ can be used as an oral therapy for of gastric inflammation.

Example 12

Immobilization of DOPA Cyclocarbonate to Gelatin for Oral Delivery

Gelatin (7.0 gm) was dissolved in hot water (100 ml) at 80-90° C., and DOPA-Cyclocarbonate (5.6 gm, 3,4-Dihydroxy-Cyclocarbonate-Phenylalanine) was added and stirred until a clear solution was formed. Cold acetone (about 4° C.) was added to co-precipitate the Gelatin and DOPA Cyclocarbonate. The supernatant fluid was removed and replaced with cold acetone (100 ml) and mixed for about 10 minutes to extract residual water from the precipitate. The supernatant fluid was again removed and replaced with fresh, cold acetone and microcrystalline cellulose (7.0 gm) and Mg Stearate (0.3 gm) were added with active mixing of the suspended powder slurry. The resulting suspension was dried under vacuum in a 60° C. bath to form a homogeneous powder, suitable for further formulation and tableting for oral administration of a dopamine metabolic precursor.

While the present invention has been disclosed with reference to certain embodiments, it will be apparent that modifications and variations are possible without departing from the spirit and scope of the invention as defined in the appended claims. Furthermore, it should be appreciated that all examples in the present disclosure, while illustrating embodiments of the invention, are provided as non-limiting examples and are, therefore, not to be taken as limiting the various aspects so illustrated. The present invention is intended to have the full scope defined by the language of the following claims, and equivalents thereof. Accordingly, the drawings and detailed description are to be regarded as illustrative and not as restrictive.

What is claimed is:

1. A method of stabilizing an active agent or drug comprising:
    providing an active agent or drug hydrate having a bound water, wherein the active agent or drug degrades in the presence of water;
    removing the bound water from the active agent or drug hydrate;
    wherein removing the bound water from the active agent or drug hydrate further comprises:
        dissolving the active agent or drug hydrate in a solvent, wherein the solvent consists of one or more independent solvents comprising 0.05% water by volume or less, wherein the solvent is capable of forming an azeotrope with a dissolved previously bound water of the active agent or drug hydrate;
        wherein dissolving the active agent or drug hydrate in the solvent forms a solution comprising the dissolved active agent or drug and an azeotrope of the solvent and the dissolved previously bound water;
        adding a substrate to the solution to form a suspension with the solution, wherein the substrate is a pharmaceutically suitable excipient; and
        sequestering the dissolved previously bound water from the active agent or drug;
        wherein sequestering the dissolved previously bound water further comprises depositing an anhydrous active agent or drug of the active agent or drug hydrate onto the substrate; and
        evaporating the azeotrope until a substrate powder is formed, wherein at least one molecule of the anhydrous active agent or drug of the substrate powder is non-covalently bound to the substrate.

2. The method of claim 1, wherein evaporating the azeotrope further comprises placing the suspension under reduced pressure or vacuum, such that removal of respective partial pressures of the solvent and the evaporated dissolved bound water are reduced thereby causing evaporation of the respective solvent and the dissolved bound water from the suspension.

3. The method of claim 1, further comprising:
replacing the reduced pressure or vacuum with an inert gas.

4. The method of claim 3, further comprising:
vacuuming away the inert gas and replacing the vacuum with a second amount of inert gas.

5. The method of claim 1 wherein evaporating further comprises subjecting the suspension to an elevated temperature.

6. The method of claim 1, further comprising:
forming a final formulation, comprising the product of the method of claim 1, into one or more dosage forms;
placing the one or more dosage forms into a container; and
filling the container with an inert gas.

7. The method of claim 1, further comprising adding a capping agent to the solvent, wherein adding the capping agent is perfouned after sequestering and before evaporating, wherein the capping agent is selected from: magnesium stearate, steric acid, stearyl fumarate, one or more peptides, or polyglutamic acid, and wherein the capping agent becomes non-covalently bound to the substrate.

8. The method of claim 1, wherein the solvent is tetrahydrofuran, ethanol, methyl ethyl ketone, ethyl acetate, or any combination thereof.

9. The method of claim 1, wherein the solvent is tetrahydrofuran.

10. The method of claim 1, wherein the solvent is ethanol.

11. The method of claim 1, wherein the active agent or drug is a thyroid hormone congener.

12. The method of claim 1, wherein the active agent or drug has high pharmacological activity when administered to an individual and therefore low mass load on the surface of the substrate when prepared for pharmaceutical use in individuals.

13. The method of claim 1, wherein the active agent or drug is selected from a hydrate of one or more of steroids, corticosteroids, cortisol, cortisone, corticosterone, hydrocortisone, prednisone, prednisolone, methylprednisolone, betamethasone, estrogen, peptide or non-steroidal hormones, insulin, thyroid hormones, thyroxine, triiodothyronine, catecholamines, catecholamine precursors, dopamine, L-DOPA, DOPA Cyclocarbonate, adrenergics, epinephrine, norepinephrine, amino acids, tyrosine, cysteine, serine, antibiotics, β-lactam antibiotics, penicillins, cephalosporins, vitamins, vitamin A, vitamin E, narcotics, opioids, methadone, morphine, amphetamine, serotonergics, serotonin, chemotherapies, cytotoxic drugs, methotrexate, oxytocin, or heparin.

14. The method of claim 1, wherein the active agent or drug is one or more iodated L-thyronine congeners.

15. The method of claim 1, wherein the active agent or drug is one or more of a L-thyroxine, a L-thyronine, or a reverse $T_3$ (3,3',5'-triiodo-L-thyronine).

16. The method of claim 1, wherein the active agent or drug is a levothyroxine.

17. The method of claim 1, wherein the substrate is cellulose, a cellulose derivative, controlled pore glass, a crystalline excipient, silica, silicate, activated carbon, or a polymer.

18. The method of claim 1, wherein the substrate is cellulose or a cellulose derivative.

19. The method of claim 3, wherein the inert gas is one or more of:
Nitrogen ($N_2$), Carbon Dioxide ($CO_2$), Argon (Ar), or Xenon (Xe).

20. The method of claim 1, wherein the amount of the active agent or drug by weight relative to the amount of the substrate by weight in the suspension is at a ratio from 1:267 to 1:2941.

21. The method of claim 1, wherein the amount of the active agent or drug by weight relative to the amount of the substrate by weight in the suspension is at a ratio of 1:267.

22. The method of claim 1, wherein the amount of the active agent or drug by weight relative to the amount of the substrate by weight in the suspension is at a ratio of 1:2941.

23. The method of claim 1, wherein simultaneously sequestering further comprises sequestering sodium away from the noncovalently bound active agent or drug.

24. The method of claim 1,
wherein the active agent or drug hydrate comprises a water of crystallization, and
wherein removing the previously bound water comprises removing the previously bound water of crystallization.

25. The method of claim 1, wherein the active agent or drug consists of a thyroid hormone congener,
wherein the substrate is cellulose or a cellulose derivative, and
wherein the solvent is tetrahydrofuran.

26. The method of claim 25, wherein the active agent or drug is a levothyroxine.

27. The method of claim 25, wherein the substrate of the substrate powder is anhydrous.

28. The method of claim 24, wherein removing the bound water further comprises removing all water of crystallization from the active agent or drug.

29. A method of stabilizing a thyroid hormone congener comprising:
forming an azeotropic solution comprising dissolving a thyroid hormone congener hydrate in a solvent, wherein the azeotropic solution comprises the thyroid hormone congener dissolved in an azeotrope, the azeotrope comprising the solvent and a previously bound water from the thyroid hormone congener hydrate;
wherein the solvent comprises 0.05% water by volume or less before forming the azeotrope, and
forming an azeotropic suspension by adding a substrate to the azeotropic solution, wherein the substrate comprises a pharmaceutically suitable excipient; and
depositing an anhydrous thyroid hormone congener onto the substrate to form a substrate powder by evaporating the azeotrope from the azeotropic suspension until the substrate powder is formed,
wherein the substrate powder comprises at least one molecule of anhydrous thyroid hormone congener that was dehydrated from of the thyroid hormone congener hydrate during evaporating the azeotrope, and
wherein the anhydrous thyroid hormone congener is non-covalently bound to the substrate.

30. The method of claim 29,
wherein the thyroid hormone congener comprises levothyroxine, and
wherein the substrate comprises cellulose or a cellulose derivative.

31. The method of claim 30,
wherein the thyroid hormone congener hydrate is levothyroxine pentahydrate.

32. The method of claim 30, wherein the solvent comprises tetrahydrofuran.

33. The method of claim 29, wherein forming the azeotropic solution comprises dissolving a salt ion from the thyroid hormone congener hydrate in the azeotrope, the method further comprising:
sequestering the salt ion onto to the substrate during evaporating the azeotrope;
wherein the thyroid hormone congener consists of a levothyroxine salt,
wherein the substrate comprises cellulose or a cellulose derivative, and
wherein the substrate powder comprises the salt ion.

34. The method of claim 33, wherein the solvent consists of tetrahydrofuran and 0.05% water by volume or less before forming the azeotropic solution.

35. The method of claim 33,
wherein the salt ion consists of a sodium ion, and
wherein the thyroid hormone congener consists of a levothyroxine.

36. The method of claim 34, wherein the thyroid hormone congener hydrate consists of levothyroxine sodium pentahydrate.

37. A sustained release composition comprising the substrate powder made by the method of claim 1.

38. The sustained release composition of claim 37, wherein the anhydrous active agent or drug is a thyroid hormone congener.

39. The sustained release composition of claim 38, wherein the thyroid hormone congener is Levothyroxine.

40. The sustained release composition of claim 38, wherein the thyroid hormone congener is Liothyronine.

41. The composition of claim 38, wherein the active agent or drug is one or more of a L-thyroxine, a L-thyronine, or a reverse $T_3$ (3,3',5'-triiodo-L-thyronine).

* * * * *